(12) United States Patent
Petersen et al.

(10) Patent No.: US 9,289,594 B2
(45) Date of Patent: Mar. 22, 2016

(54) LEADS INCORPORATING A LASER PROCESSED ELECTRODE

(71) Applicant: Cardiac Pacemakers, Inc., St. Paul, MN (US)

(72) Inventors: Eric M. Petersen, Maple Grove, MN (US); Steven R. Larsen, Lino Lakes, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 135 days.

(21) Appl. No.: 14/016,808

(22) Filed: Sep. 3, 2013

(65) Prior Publication Data

US 2014/0067031 A1    Mar. 6, 2014

Related U.S. Application Data

(60) Provisional application No. 61/697,658, filed on Sep. 6, 2012.

(51) Int. Cl.
*A61N 1/05* (2006.01)
*A61B 5/04* (2006.01)
*B23K 26/00* (2014.01)
*B23K 26/36* (2014.01)
*B23K 26/40* (2014.01)

(52) U.S. Cl.
CPC .............. *A61N 1/05* (2013.01); *B23K 26/0006* (2013.01); *B23K 26/0084* (2013.01); *B23K 26/0624* (2015.10); *B23K 26/362* (2013.01); *B23K 26/40* (2013.01); *A61N 1/056* (2013.01); *A61N 1/0551* (2013.01); *B23K 2203/04* (2013.01); *B23K 2203/08* (2013.01); *B23K 2203/14* (2013.01); *B23K 2203/50* (2015.10)

(58) Field of Classification Search
USPC .......................................... 600/373; 607/116
See application file for complete search history.

(56) References Cited

U.S. PATENT DOCUMENTS

2013/0296678 A1* 11/2013 Larsen et al. ................. 600/373

OTHER PUBLICATIONS

Tan, B. et al., "A femtosecond laser-induced periodical surface structure on crystalline silicon", J. Micromech. Microeng., vol. 16, 2006, pp. 1-6.

* cited by examiner

*Primary Examiner* — Carl H Layno
*Assistant Examiner* — Jon Eric C Morales
(74) *Attorney, Agent, or Firm* — Faegre Baker Daniels LLP

(57) ABSTRACT

Medical devices may include an electrode that has been processed to increase its surface area. In some cases, an electrode may be processed using an ultrafast laser to produce an electrode surface that includes macrostructures formed within the electrode surface and nanostructures formed on the macrostructures. The nanostructures may be formed of material that was removed from the electrode surface in forming the macrostructures.

5 Claims, 9 Drawing Sheets

LEADS INCORPORATING A LASER PROCESSED ELECTRODE

CROSS-REFERENCE TO RELATED APPLICATIONS

This application claims the benefit under 35 U.S.C. section 119(e) to U.S. Provisional Application 61/697,658, entitled "LEADS INCORPORATING A LASER PROCESSED ELECTRODE", filed on Sep. 6, 2012, which is herein incorporated by reference in its entirety.

TECHNICAL FIELD

The present invention relates to medical devices and methods for forming medical devices. More specifically, the invention relates to an electrode, an implantable lead incorporating the electrode and a method of processing the electrode.

BACKGROUND

Implantable medical devices, such as electrical stimulators or sensors, are used in a variety of therapeutic applications. In some implantable medical devices, an electrical stimulator or sensor delivers electrical pulses to a target tissue site within a patient with the aid of one or more medical leads. The medical leads are coupled to the implantable medical device at one end while the other end carrying electrodes is placed at the target tissue site. The electrodes may be used in stimulating and/or sensing applications.

The ability of an electrode to transfer current is related to its conductivity and its surface area. As electrodes become smaller in size, there is a corresponding reduction in surface area and thus the ability of the electrode to transfer current. Thus, there is a need for an electrode and a medical lead including an electrode that is capable of providing desired current transfer even as the size of the electrode decreases.

SUMMARY

The present invention pertains to an electrode that has been processed to increase its surface area as well as to a medical lead that includes such an electrode. In some embodiments, an electrode may be processed using an ultrafast laser to produce an electrode surface that includes macrostructures formed within the electrode surface and nanostructures formed on the macrostructures. The nanostructures may be formed of material that was removed from the electrode surface in forming the macrostructures.

Accordingly, Example 1 is an implantable medical lead that includes an elongate lead body and an electrical conductor that extends through the elongate lead body from a proximal region to a distal region thereof. An electrode is secured to the distal region of the elongate lead body. The electrode includes a metallic base having an outer surface, a plurality of macrostructures that are disposed within the outer surface of the metallic base and a plurality of nanostructures that are disposed on the plurality of macrostructures. At least some of the plurality of macrostructures have an average major dimension that is in the range of about 5 micrometers to about 200 micrometers. At least some of the plurality of nanostructures have an average major dimension that is in the range of about 100 nanometers to about 2 micrometers.

Example 2 includes Example 1 and further includes a plurality of valleys that are formed in the outer surface such that the plurality of macrostructures are hills disposed between adjacent valleys.

Example 3 includes any of Examples 1 and 2 and specifies that the plurality of nanostructures are formed of the same material as the material forming the metallic base.

Example 4 includes any of Examples 1-3 and specifies that the plurality of nanostructures are formed of material removed from the metallic base in forming the plurality of valleys.

Example 5 includes any of Examples 1-4 and specifies that at least some of the plurality of macrostructures have an average major dimension to average minor dimension aspect ratio that is in the range of about 1:1 to about 20:1.

Example 6 includes any of Examples 1-5 and specifies that at least some of the plurality of nanostructures have an average major dimension to average minor dimension aspect ratio that is in the range of about 1:1 to about 20:1.

Example 7 includes any of Examples 1-6 and specifies that the metallic base of the electrode includes a biocompatible material.

Example 8 includes any of Examples 1-7 and specifies that the metallic base includes a material selected from the group consisting of titanium, titanium alloys, stainless steel and platinum-iridium alloys.

Example 9 includes any of Examples 1-7 and specifies that the metallic base includes a noble metal.

Example 10 includes any of Examples 1-9 and specifies that the electrode is a ring electrode.

Example 11 includes any of Examples 1-9 and specifies that the electrode is a sheet electrode.

Example 12 is a method of preparing an electrode for use with an implantable medical lead. Macrostructures are formed in a metallic surface of the electrode by removing material from the metallic structure, the macrostructures having an average major dimension that is in the range of about 5 micrometers to about 200 micrometers. Nanostructures are formed by depositing removed material on the macrostructures, the nanostructures having an average major dimension that is in the range of about 100 nanometers to about 2 micrometers.

Example 13 includes Example 12 and specifies that the macrostructures have an average major dimension to average minor dimension aspect ratio that is in the range of about 1:1 to about 20:1.

Example 14 includes any of Examples 12-13 and specifies that the nanostructures have an average major dimension to average minor dimension aspect ratio that is in the range of about 1:1 to about 20:1.

Example 15 includes any of Examples 12-14 and specifies that forming macrostructures on the metallic surface by material removal includes subjecting the metallic surface to an ultrafast laser having a pulse width of less than about 15 picoseconds.

Example 16 includes Example 15 and specifies that subjecting the metallic surface to an ultrafast laser strips electrons from the metallic surface and produces a positively charged surface that subsequently results in a Coulomb explosion.

Example 17 includes any of Examples 15-16 and specifies that forming nanostructures includes forming nanostructures from material ejected from the metallic surface during the Coloumb explosion.

Example 18 is an electrode for use with an implantable lead. The electrode includes a metallic surface and a plurality of macrostructures disposed within the metallic surface. A plurality of nanostructures are disposed on the plurality of macrostructures. The plurality of macrostructures are defined at least in part by a plurality of voids dispersed between the plurality of macrostructures and at least some of the plurality of macrostructures having an average major dimension that is in the range of about 5 micrometers to about 200 micrometers. At least some of the plurality of nanostructures have an average major dimension that is in the range of about 100 nanometers to about 2 micrometers. The plurality of voids are formed by removing material from the metallic surface, and at least some of the plurality of nanostructures include removed material.

Example 19 includes Example 18 and specifies that at least some of the plurality of macrostructures have an average major dimension to average minor dimension aspect ratio that is in the range of about 1:1 to about 20:1 and at least some of the plurality of nanostructures have an average major dimension to average minor dimension aspect ratio that is in the range of about 1:1 to about 20:1.

Example 20 includes any of Examples 18-19 and specifies that the metallic base of the electrode includes a material selected from the group consisting of titanium, stainless steel and platinum-iridium alloys.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

Figure 1:
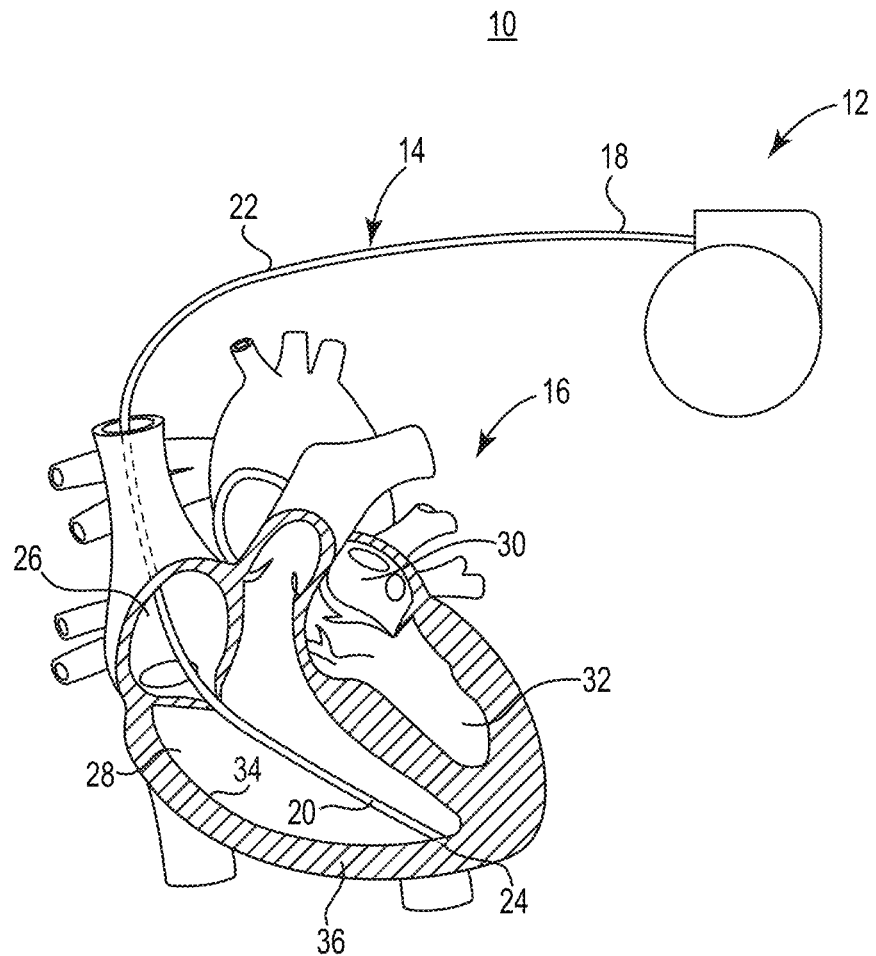
FIG. 1 is a schematic view of an implantable medical device in a cardiac rhythm management (CRM) system in accordance with embodiments of the present invention.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

Figure 2:
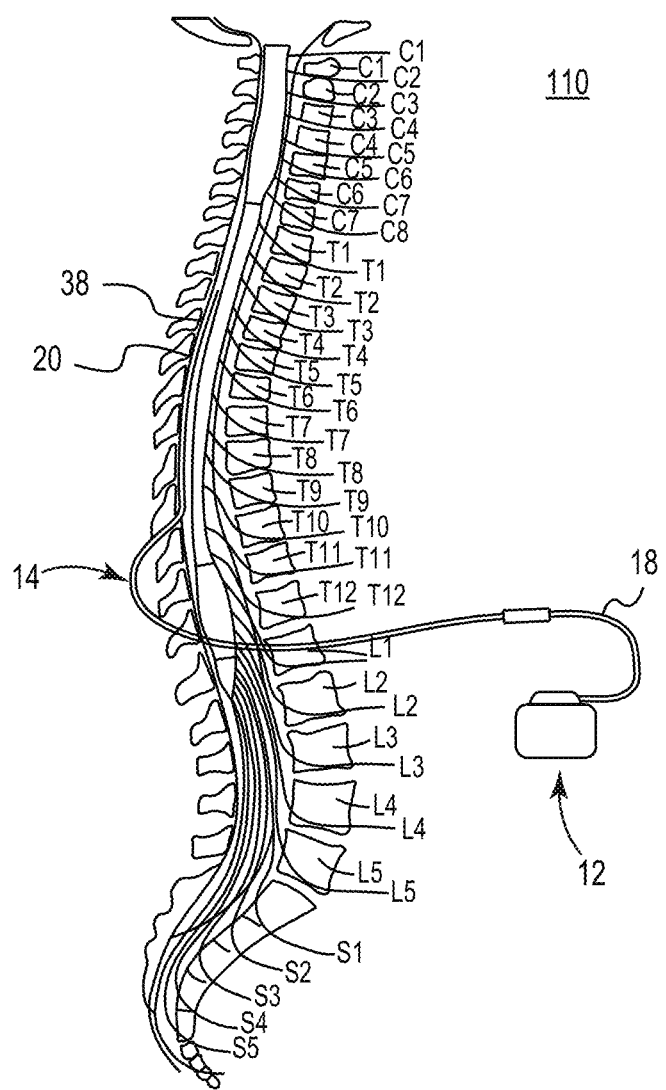
FIG. 2 is a schematic view of an implantable medical device in a neurostimulation system in accordance with embodiments of the present invention.

FIGS. 1 and 2 provide illustrative but non-limiting examples of medical applications utilizing implantable medical leads. In particular, FIGS. 1 and 2 demonstrate particular anatomical locations within the body in which an implantable medical lead can be used. These locations are illustrative only, as implantable medical leads can be used in a variety of additional anatomical locations.

FIG. 1 is a schematic view of an implantable cardiac rhythm management (CRM) system 10. As shown, the system 10 includes an implantable pulse generator (IPG) 12 and an implantable lead 14, which extends from a proximal region 18 to a distal region 20, and which includes a lead body 22. As shown in FIG. 1, the heart 16 includes a right atrium 26, a right ventricle 28, a left atrium 30 and a left ventricle 32. It can be seen that the heart 16 includes an endocardium 34 covering the myocardium 36. In some embodiments, as illustrated, a fixation helix 24, located at the distal region 20 of the lead 14, penetrates through the endocardium 34 and is embedded within the myocardium 36. In some embodiments, the fixation helix 24 is electrically active and thus operates as a helical electrode 38 for sensing the electrical activity of the heart 16 and/or applying a stimulating pulse to the right ventricle 28. In some embodiments, the CRM system 10 includes a plurality of leads 14. For example, it may include a first lead 14 adapted to convey electrical signals between the IPG 12 and the right ventricle 28 and a second lead (not shown) adapted to convey electrical signals between the IPG 12 and the right atrium 26 or coronary veins (not shown).

FIG. 2 is a schematic view of a representative implantable neurostimulation (e.g., spinal cord stimulation) system 110. As shown in FIG. 2, the neurostimulation system 110 includes an IPG 12, which generates electrical stimulation pulses, and a lead 14 extending from the IPG 12 to a desired stimulation site. The lead portion 14 has a proximal region 18 and a distal region 20 and includes an electrode 38 or plurality of electrodes 38 at or near the distal region 20. As further shown in FIG. 2, C1-C8 are the cervical vertebrae and nerves, T1-T12 are the thoracic vertebrae and nerves, L1-L5 are the lumbar vertebrae and nerves, and S1-S5 are the sacrum and coccyx and the sacral nerves. Other implantable neurostimulation systems include deep brain stimulation and peripheral (e.g., vagal) nerve stimulation systems.

Figure 3:
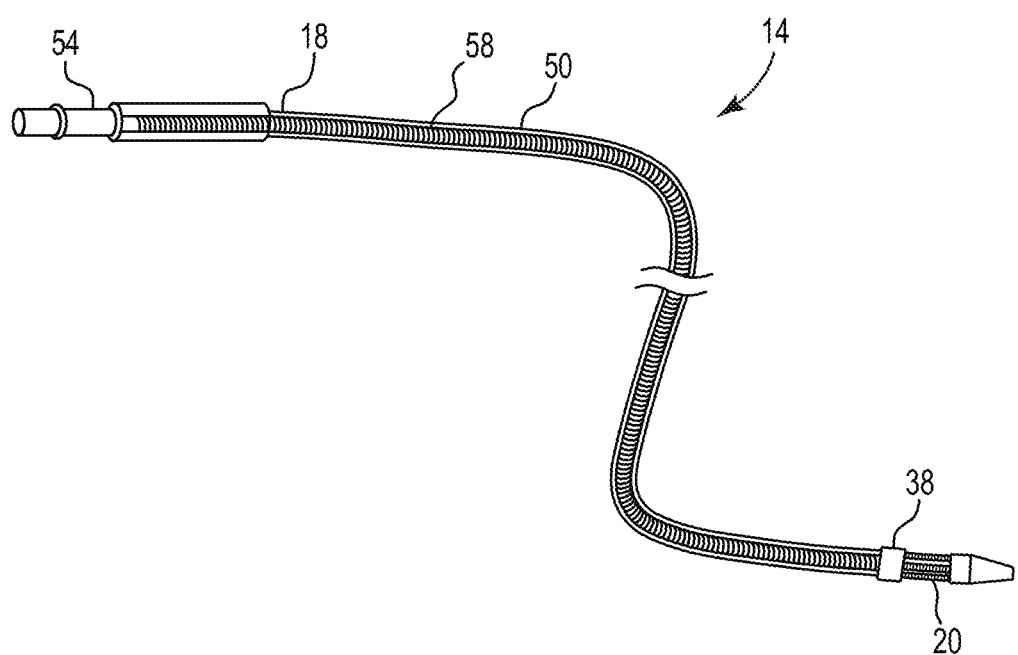
FIG. 3 is a schematic view of a medical electrical lead in accordance with embodiments of the present invention.

FIG. 3 is a schematic view of a medical electrical lead 14. The lead 14 is adapted to deliver electrical pulses to stimulate a heart 16 or nervous system and/or to receive electrical pulses to monitor the heart 16 or nervous system. According to some embodiments, the lead 14 can be sized and configured to be delivered near the vagus nerve, the peripheral nerves, the spinal cord, or the heart 16. The medical electrical lead 14 includes an elongated lead body 50 having opposed proximal and distal regions 18 and 20. The lead body 50 can be formed from a bio-compatible insulative material, for example, silicone rubber, polyurethane, or the like. A connector 54 is operatively associated with the proximal region 18 of the lead body 50. The connector 54 may be of a standard type, size or configuration. Connector 54 can be electrically connected to the electrode 38 by way of a conductor coil 58 that extends through the interior lumen of lead body 50. Conductor coil 58 can be generally helical in configuration and can include one or more conductive wires or filaments. At least one electrode 38 can be operatively associated with the distal region 20 of the lead body 50. The electrode 38 can be formed from one or more conductive materials. Examples of conductive materials include, but are not limited to, platinum, stainless steel, nitinol, MP35N, titanium, a platinum-iridium alloy, and combinations thereof. In some embodiments, the electrode 38 is disposed proximal to the distal region 20 of the lead 14. Alternatively, the electrode 38 can be located along the lead body 50 between the proximal region 18 and the distal region 20. According to yet another embodiment, the electrode 38 can be a tip electrode. A tip electrode is located at the very distal portion of the distal region 20 of the lead body 50 and is commonly employed in left ventricular leads. Multiple electrodes 38 may also be utilized according to some embodiments.

Figure 4:
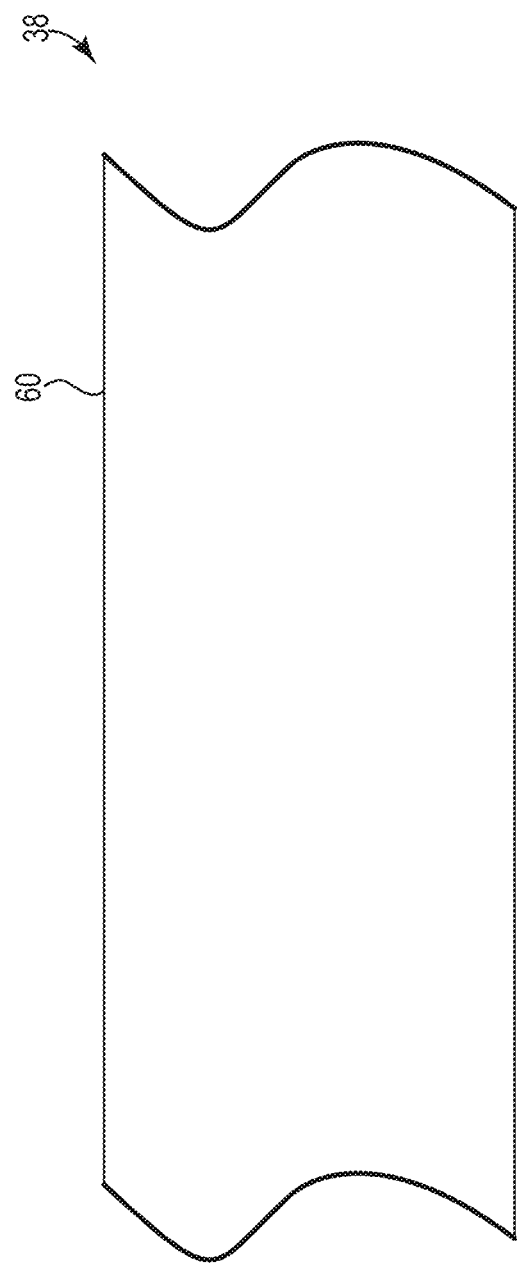
FIG. 4 is a schematic view of a portion of an electrode in accordance with embodiments of the present invention.

In some embodiments, the electrode 38 may be treated or otherwise processed to increase the surface area of the electrode 38. FIG. 4 is a schematic illustration of a portion of the electrode 38 having a surface 60. The electrode 38 may be any desired type of electrode. In some embodiments, the electrode 38 may represent a ring electrode. In some embodiments, the electrode 38 may represent a sheet electrode. In some embodiments, the electrode 38 may represent a flexible sheet electrode such as may be used in vagus nerve stimulation. In some embodiments, as seen in FIG. 5, the electrode 38 may be processed such that macrostructures 62 are formed in or on the surface 60 of the electrode 38.

The electrode 38 may be formed of a variety of different materials. In some embodiments, the electrode 38 may include a base that is formed of a metallic material. The electrode 38 may be formed of a biocompatible metal or metal alloy. In some embodiments, the electrode 38 may be formed of or otherwise include a noble metal such as gold, platinum, iridium, palladium, osmium, silver, rhodium and ruthenium. In some embodiments, the electrode 38 may be formed of or otherwise include titanium, titanium alloys, platinum-iridium alloys or stainless steel. In some cases, the electrode 38 may have a layered structure including a base material and one or more additional materials coated onto the base material. The base material and the one or more additional materials may be independently selected from the materials described herein.

Figure 5:
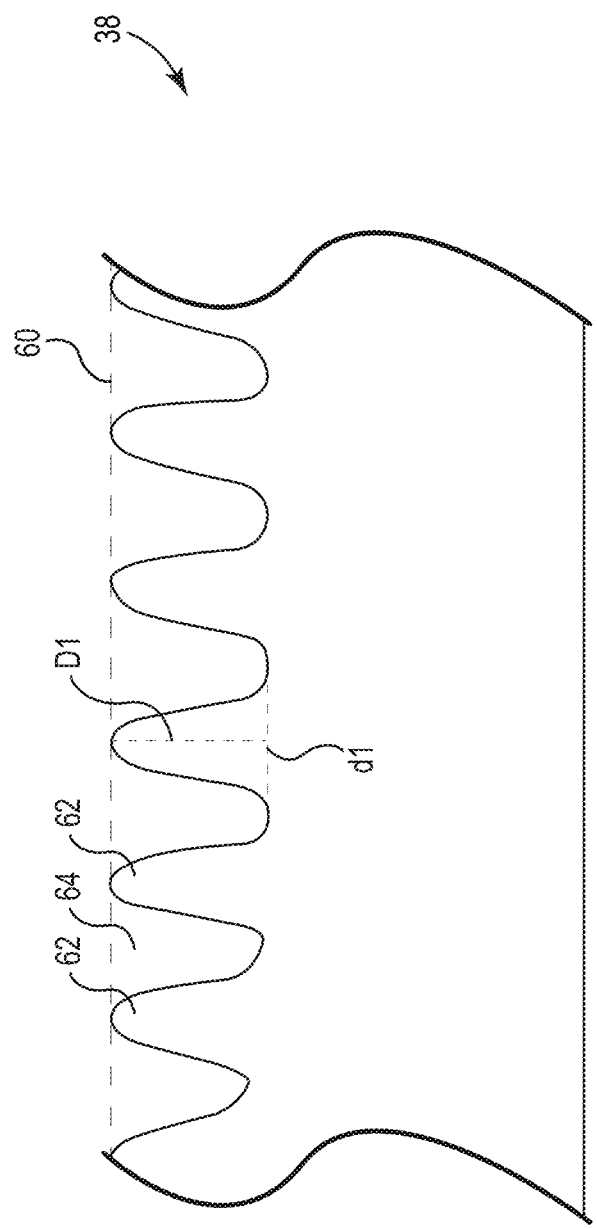
FIG. 5 is a schematic view of a portion of an electrode in accordance with embodiments of the present invention.

FIG. 5 is a schematic illustration of a portion of the electrode 38. The macrostructures 62 are disposed between adjacent valleys 64. In some instances, the valleys 64 may be considered as defining the macrostructures 62, as the valleys 64 extend downward from the surface 60 (shown in phantom). In some embodiments, the macrostructures 62 do not extend above or at least do not substantially extend above the surface 60. While the macrostructures 62 may vary somewhat in size and shape, the macrostructures 62 may be considered as having a major dimension D1 and a minor dimension (perpendicular to the major dimension) d1. In some embodiments, at least some of the macrostructures 62 may be considered as having an average aspect ratio (D1:d1) that is in the range of about 1:1 to about 20:1.

Figure 6:
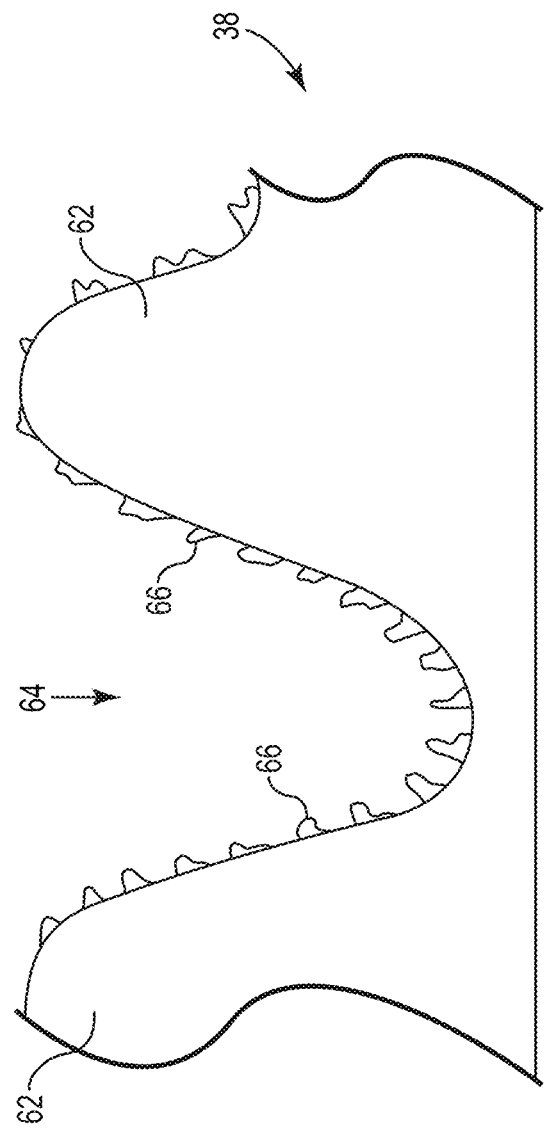
FIG. 6 is a schematic view of a portion of an electrode in accordance with embodiments of the present invention.

In some embodiments, at least some of the macrostructures 62 may have a major dimension D1 that is in the range of about 5 micrometers to about 200 micrometers. In some embodiments, as shown in FIG. 6, nanostructures 66 may be formed on the macrostructures 64. It will be appreciated that the complex surface structure including macrostructures 62 and nanostructures 66 will provide a greatly increased surface area and hence improved current transfer.

Figure 7:
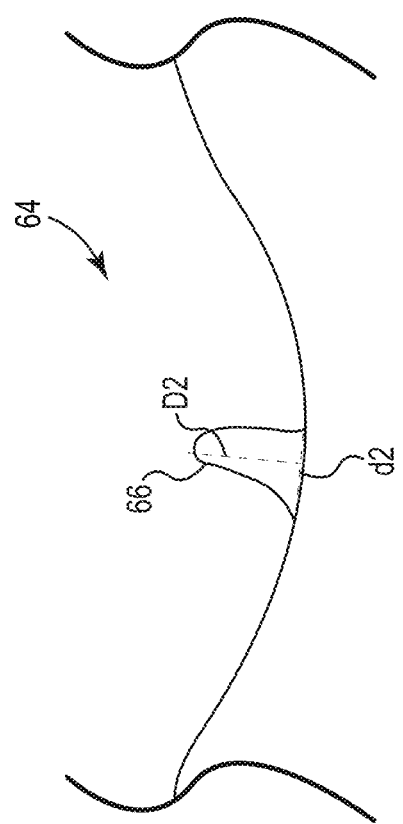
FIG. 7 is a schematic view of a portion of an electrode in accordance with embodiments of the present invention.

FIG. 6 is a schematic illustration of a portion of the electrode 38 showing nanostructures 66. It will be appreciated that inclusion of the nanostructures 66 may substantially increase the surface area of the electrode 38, and thus substantially increase the ability of the electrode 38 to transfer current in either a sensing application or a shocking application. While the nanostructures 66 may vary in size and shape, in some embodiments, as shown in FIG. 7, at least some of the nanostructures 66 may be considered as having a major dimension D2 and a minor dimension (perpendicular to the major dimension) d2. In some embodiments, at least some of the nanostructures 66 may be considered as having an average aspect ratio (D2:d2) that is in the range of about 1:1 to about 20:1. In some embodiments, at least some of the nanostructures 66 may have a major dimension D2 that is in the range of about 100 nanometers to about 2 micrometers.

In some embodiments, an ultrafast laser may be used to remove material from the surface 60 of the electrode 38 in order to form the macrostructures 62. In some embodiments, an ultrafast laser is a laser configured to provide a short pulse width, such as a pulse width of about 15 picoseconds or less. In some instances, the valleys 64 are formed by laser removal of the material. By subjecting the surface 60 of the electrode 38 to a laser having a pulse width of about 15 picoseconds or less, in some instances about 10 picoseconds or less, nonlinear effects can occur. When a metal surface is subjected to incident light, such as from a laser beam, some of the incident energy is transferred to free electrons in the metal surface. If the incident light is sufficiently short in duration, at least some of the free electrons may be ejected from the metal surface before the excited electrons have time to transfer energy to the surrounding metal lattice (crystal structure) in the form of thermal energy.

As the free electrons are ejected from the surface 60, the surface 60 will be positively charged as a result of losing negatively charged electrons. The positively charged atoms within the surface 60 will repel each other. In some embodiments, this may result in what is known as a Coulomb explosion in which some of the positively charged atoms are expelled from the surface 60.

As the positively charged atoms redeposit themselves, the nanostructures 66 can be formed. Accordingly, in some embodiments, the nanostructures 66 are formed from material that is removed from the surface 60 in forming the macrostructures 62. In some embodiments, the nanostructures 66 can be formed of the same metal or other material that forms the electrode 38.

In some embodiments, the ultrafast laser used to produce the macrostructures 62 and the nanostructures 66 may have a spot size of less than about 0.001 inches and a pulse width of about 800 femtoseconds. The linear pulse spacing (velocity/pulse frequency) and pulse energy can vary depending on the specific macrostructures 62 and/or nanostructures 66 that are desired. For example, when operating the laser at a pulse energy of about 10 micro Joules and a pulse spacing of about 5 microns, only macrostructures 62 will be produced. If the laser is operated at a pulse energy of about 2 micro Joules and a pulse spacing of about 0.75 microns, nanostructures 66 will also be produced.

In some embodiments, the complex surface structure may subsequently be coated with materials that provide the electrode with desired characteristics. In some instances, the complex surface structure enhances adhesion of the coating material, particularly in cases where the electrode is flexible.

Illustrative but non-limiting examples of materials that may be used as coating materials include platinum black, iridium oxide, titanium nitride and titanium carbide. Platinum black is a fine black powder of metallic platinum. Iridium oxide, titanium nitride and titanium carbide are further examples of conductive biocompatible materials. These materials, if present, may be added by sintering, plating, material deposition, chemical vapor deposition, physical vapor deposition or atomic layer deposition techniques, and may be added either before or after laser treatment.

Figure 8:
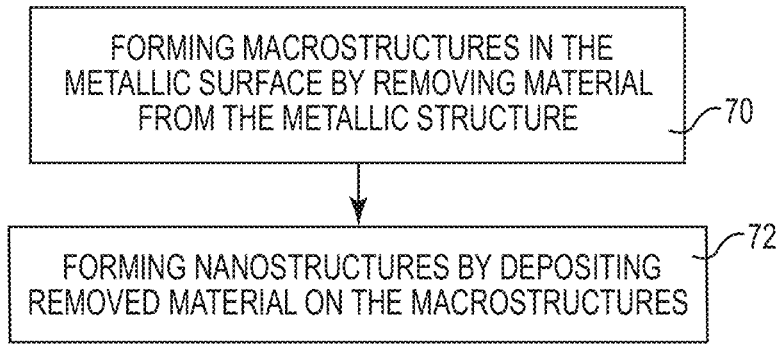
FIG. 8 is a flow diagram illustrating a method in accordance with embodiments of the present invention.

FIG. 8 is a flow diagram of an illustrative but non-limiting example of a method of processing an electrode surface to increase the surface area of the electrode surface. In some embodiments, this method may be carried out using an ultrafast laser having a pulse width of less than about 15 picoseconds. Macrostructures may be formed in the metallic surface of the electrode by removing material from the metallic surface, as generally indicated at block 70. In some instances, the macrostructures may be at least partially defined by voids or valleys created in the metallic surface as material is removed. At least some of the removed material may be deposited onto the macrostructures to form nanostructures, as generally indicated at block 72.

Figure 9:
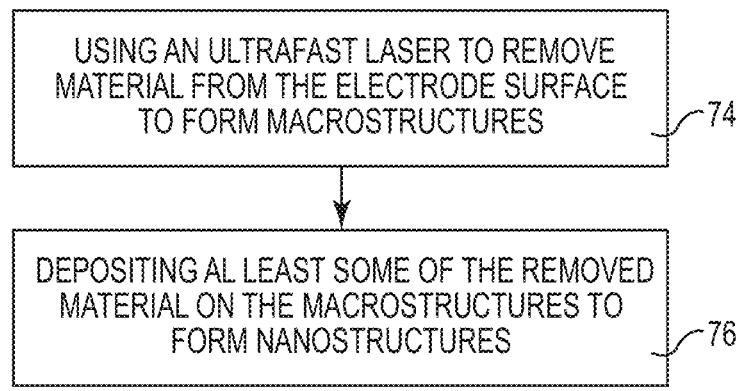
FIG. 9 is a flow diagram illustrating a method in accordance with embodiments of the present invention.

FIG. 9 is a flow diagram of an illustrative but non-limiting example of a method of processing an electrode surface to increase the surface area of the electrode surface. Macrostructures may be formed in the metallic surface of the electrode by removing material from the metallic surface using an ultrafast laser, as generally indicated at block 74. In some instances, the macrostructures may be at least partially defined by voids or valleys created in the metallic surface as material is removed. At least some of the removed material may be deposited onto the macrostructures to form nanostructures, as generally indicated at block 76.

Figure 10:
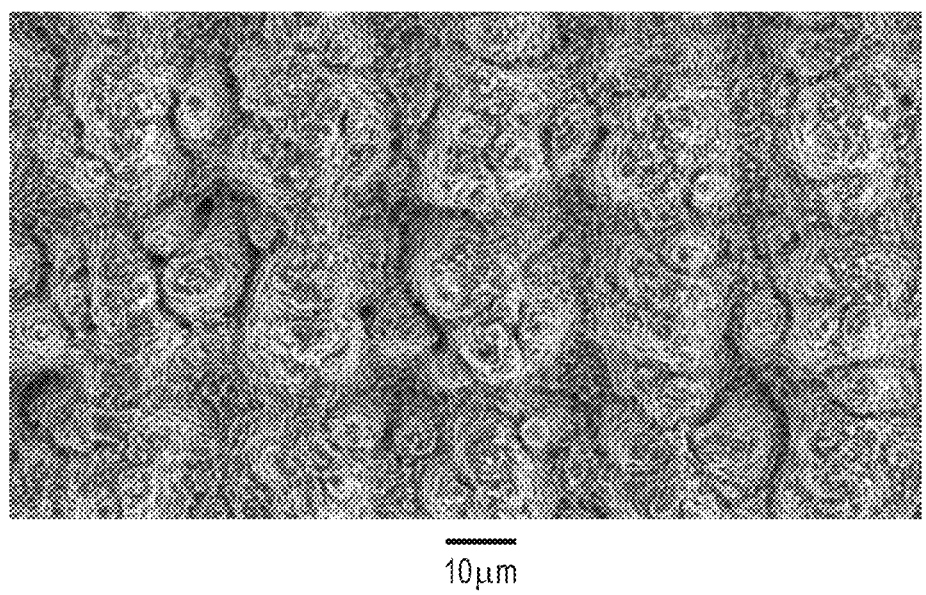
FIG. 10 is an SEM image of a stainless steel surface including macrostructures and nanostructures in accordance with embodiments of the present invention.

FIG. 10 is an SEM image of a stainless steel surface that was laser processed in the manner described herein. As can be seen, the stainless steel surface includes both macrostructures and nanostructures formed on the macrostructures. The process parameters used to process the stainless steel surface are outlined in the Table below:

| | |
|---|---|
| spot size | 25 microns |
| scan velocity | 500 mm/s |
| frequency | 600 Hz |
| laser wavelength | 1.552 microns |
| laser pulse width | 800 femtoseconds |
| pulse energy | 3 micro Joules |
| line spacing | 25 microns between lines |

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

We claim:

1. A method of preparing an electrode for use with an implantable medical lead, the electrode including a metallic surface, the method comprising:
    forming macrostructures in the metallic surface by removing material from the metallic structure, the macrostructures having an average major dimension that is in the range of about 5 micrometers to about 200 micrometers including subjecting the metallic surface to an ultrafast laser having a pulse width of less than about 15 picoseconds; and
    forming nanostructures by redepositing removed material on the macrostructures resulting from the forming of the macrostructures, the nanostructures having an average major dimension that is in the range of about 100 nanometers to about 2 micrometers.

2. The method of claim 1, wherein the macrostructures have an average major dimension to average minor dimension aspect ratio that is in the range of about 1:1 to about 20:1.

3. The method of claim 1, wherein the nanostructures have an average major dimension to average minor dimension aspect ratio that is in the range of about 1:1 to about 20:1.

4. The method of claim 1, wherein subjecting the metallic surface to an ultrafast laser strips electrons from the metallic surface and produces a positively charged surface that subsequently results in a Coloumb explosion.

5. The method of claim 4, wherein forming nanostructures comprises forming nanostructures from material ejected from the metallic surface during the Coloumb explosion.

* * * * *